(12) United States Patent
Wiles et al.

(10) Patent No.: US 8,835,456 B1
(45) Date of Patent: Sep. 16, 2014

(54) NS5A INHIBITORS USEFUL FOR TREATING HCV

(75) Inventors: Jason Allan Wiles, Madison, CT (US); Venkat Gadhachanada, Hamden, CT (US); Avinash Phadke, Branford, CT (US); Milind Deshpande, Madison, CT (US); Dawei Chen, Middletown, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 235 days.

(21) Appl. No.: 13/423,935

(22) Filed: Mar. 19, 2012

Related U.S. Application Data

(60) Provisional application No. 61/454,234, filed on Mar. 18, 2011.

(51) Int. Cl.
*A61K 31/44* (2006.01)
*C07D 451/02* (2006.01)

(52) U.S. Cl.
USPC .......................... 514/304; 546/124

(58) Field of Classification Search
USPC .......................... 546/124; 514/304
See application file for complete search history.

(56) References Cited

U.S. PATENT DOCUMENTS

| | | | |
|---|---|---|---|
| 7,906,619 | B2 | 3/2011 | Phadke et al. |
| 8,088,368 | B2 | 1/2012 | Guo et al. |
| 2007/0004711 | A1 | 1/2007 | Zhang et al. |
| 2008/0050336 | A1 | 2/2008 | Bachand et al. |
| 2010/0152103 | A1 | 6/2010 | Phadke et al. |
| 2010/0158862 | A1 | 6/2010 | Kim et al. |
| 2010/0216735 | A1 | 8/2010 | Lechleiter |
| 2010/0310512 | A1 | 12/2010 | Guo et al. |
| 2011/0064698 | A1* | 3/2011 | Or et al. .................. 424/85.5 |

FOREIGN PATENT DOCUMENTS

| | | |
|---|---|---|
| WO | 2008021927 A2 | 2/2008 |
| WO | 2010111483 A1 | 9/2010 |
| WO | 2011031904 A1 | 3/2011 |
| WO | 2011091532 A1 | 8/2011 |

OTHER PUBLICATIONS

U.S. Appl. No. 61/567,216, filed with the USPTO on Dec. 6, 2011.

\* cited by examiner

*Primary Examiner* — Niloofar Rahmani
(74) *Attorney, Agent, or Firm* — Cantor Colburn LLP

(57) ABSTRACT

The invention provides compounds of Formula I

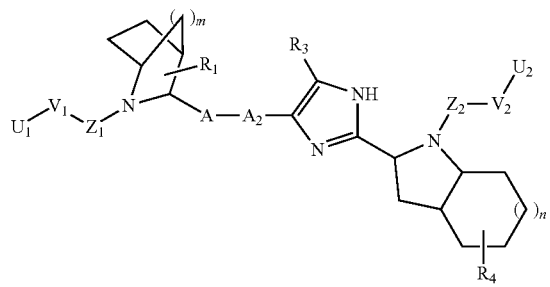

(Formula I)

and the pharmaceutically salts thereof. These compounds may be generally described as bridged-bicyclo indole-containing compounds. The variables shown in Formula I are defined herein. Certain compounds of Formula I are useful as antiviral agents. Compounds as disclosed herein are potent and/or selective inhibitors of viral replication, particularly Hepatitis C virus replication. The invention also provides pharmaceutical compositions containing one or more compounds of Formula I and at least one pharmaceutically acceptable carrier. Such pharmaceutical compositions may contain a compound of Formula I as the only active agent or may contain a combination of a compound of Formula I and one or more other pharmaceutically active agents. The invention also provides methods for treating viral infections, including Hepatitis C infections, in patients.

14 Claims, No Drawings

NS5A INHIBITORS USEFUL FOR TREATING HCV

CROSS REFERENCES TO RELATED APPLICATION

This application claims priority from U.S. Provisional Application No. 61/454,234, filed Mar. 18, 2011, which is hereby incorporated by reference in its entirety.

FIELD OF THE INVENTION

The present disclosure provides compounds of Formula I, which may be generally described as bridged-bicyclo indole-containing compounds, useful as antiviral agents. Certain compounds of Formula I disclosed herein are potent and/or selective inhibitors of viral replication, particularly Hepatitis C virus replication. The invention also provides pharmaceutical compositions containing one compounds of Formula I and one or more pharmaceutically acceptable carriers. Such pharmaceutical compositions may contain a compound of Formula I as the only active agent or may contain a combination of a compound of Formula I and one or more other pharmaceutically active agents. The disclosure also provides methods for treating viral infections, including Hepatitis C infections.

BACKGROUND

An estimated 3% of the world's population is infected with the hepatitis C virus. Of those exposed to HCV, 80% to 85% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will spontaneously clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:
NH2-C-E1-E2-p7-NS2-NS3-NS4A-NS4B—NS5A-NS5B—COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B—NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Antiviral agents such as BI 201335 (Boehringer Ingelheim), TMC435 (Tibotec), Telaprevir (Vertex), and Boceprevir (Merck) may be used for treatment of chronic HCV, Several antiviral agents including ACH-1625, ACH-2684, ACH-2928, and ACH-3102 are in clinical development for treatment of chronic HCV. Each of these drugs may be used in combination with a compound of /Formula I, discussed below, and optionally in combination with an immune modulator, such as interferon, or an additional anti-viral agent. Due to lack of effective therapies for treatment for certain HCV strains and the high mutation rate of HCV, new therapies are needed. The present invention fulfills this need and provides additional advantages, which are described herein.

SUMMARY OF THE INVENTION

The invention provides compounds of Formula I (shown below) and includes bridged-bicyclo indole-containing compounds. The compounds of Formula I disclosed herein possess antiviral activity. The invention provides compounds of Formula I that are potent and/or selective inhibitors of Hepatitis C virus replication. Without wishing to be bound to any particular theory it is believed that compounds of Formula I act as specific inhibitors of NS5a, an HCV RNA binding protein. The disclosure also provides pharmaceutical compositions containing one or more compound of Formula I, or a salt, solvate, or prodrug of such a compound, and one or more pharmaceutically acceptable carriers.

The disclosure further comprises methods of treating patients suffering from certain infectious diseases by providing to such patients an amount of a compound of Formula I effective to reduce signs or symptoms of the disease or disorder. These infectious diseases include viral infections, particularly HCV infections. The disclosure particularly includes methods of treating human patients suffering from an infectious disease, but also encompasses methods of treating other animals, including livestock and domesticated companion animals, suffering from an infectious disease.

Methods of treatment include providing a compound of Formula I as a single active agent or providing a compound of Formula I in combination with one or more other therapeutic agents.

Thus in a first aspect the invention includes compounds of Formula I pharmaceutically acceptable salts thereof:

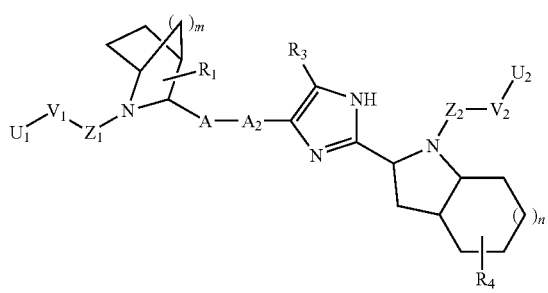

Formula I

Within Formula I the variables carry the following values:
m is 1 or 2; and n is 0, 1, or 2.
A is a group of the formula

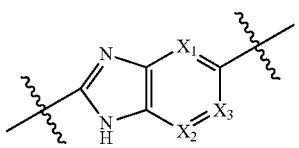

or

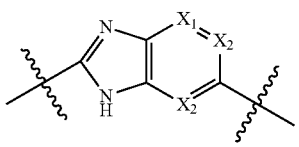

where $X_1$, $X_2$, and $X_3$ are independently N or CH, where each CH is unsubstituted or substituted with a substituent independently chosen from hydroxyl, halogen, $C_1$-$C_2$alkyl, and $C_1$-$C_2$alkoxy; or A is a group of the formula

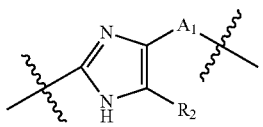

where
$A_1$ and $A_2$ are independently chosen from phenyl, pyridyl, thienyl, benzylfuranyl, and pyrimidinyl, each of which is unsubstituted or substituted with one or more substituents independently chosen from amino, cyano, hydroxyl, halogen, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy.

$U_1$ and $U_2$ are independently chosen from:
hydrogen, $C_2$-$C_6$alkanoyl, $C_1$-$C_6$alkylester, mono- and di-$C_1$-$C_6$alkylcarbamate, mono- and di-$C_1$-$C_6$alkylcarboxamide, mono- and di-$C_1$-$C_6$alkylsulfonamide, and $C_1$-$C_6$alkylsulfonamide; each of which $U_1$ and $U_2$ other than hydrogen is unsubstituted or substituted with 1 or more substituents independently chosen from amino, cyano, hydroxyl, halogen, mono- and di-$C_1$-$C_4$alkylamino, $C_1$-$C_4$alkoxy, $C_1$-$C_2$haloalkyl, and $C_1$-$C_2$haloalkoxy;

$V_1$ and $V_2$ are independently chosen $C_1$-$C_4$alkylene, each of which is unsubstituted or substituted with one or more substituents independently chosen from amino, cyano, hydroxyl, halogen, $C_1$-$C_6$alkyl, $C_1$-$C_6$alkoxy, mono- and di-$C_1$-$C_4$alkylamino, $(C_3$-$C_7$cycloalkyl)$C_0$-$C_4$alkyl, $C_1$-$C_2$haloalkyl, and $C_1$-$C_2$haloalkoxy;

$Z_1$ and $Z_2$ are independently chosen from —$SO_2$—, —$NHSO_2$, —(C=O)—, —(C=O)O—, —NH—, and —(C=O)NH—, each of which may be in either orientation;

$R_1$ is absent or $R_1$ is one or more substituents independently chosen from hydroxyl, halogen, $C_1$-$C_2$alkyl, and $C_1$-$C_2$alkoxy;

$R_2$ and $R_3$ are independently chosen from hydrogen, from hydroxyl, halogen, $C_1$-$C_2$alkyl, and $C_1$-$C_2$alkoxy;

$R_4$ is absent or $R_4$ is one or more substituents present on either ring of the bicyclic system on which it is shown, which substituents are independently chosen from hydroxyl, halogen, $C_1$-$C_2$alkyl, and $C_1$-$C_2$alkoxy; and $A_1$ and $A_2$ are independently chosen from phenyl, pyridyl, thiophenyl, and pyrimidinyl, each of which is unsubstituted or substituted with one or more substituents independently chosen from amino, cyano, hydroxyl, halogen, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy.

Certain compounds of Formula I disclosed herein exhibit good activity in an HCV replication assay, such as the HCV replicon assay set forth in Example 3, which follows. Preferred compounds of Formula I exhibit an $EC_{50}$ of about 1 micromolar or less, or more preferably an $EC_{50}$ of about 10 nanomolar or less; or still more preferably an $EC_{50}$ of about 1 nanomolar or less in an HCV replicon replication assay.

DETAILED DESCRIPTION OF THE INVENTION

Chemical Description and Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well hydrates of the compound and all pharmaceutically acceptable salts of the compound.

The term "Formula I" encompasses all compounds that satisfy Formula I, including any enantiomers, racemates and stereoisomers, as well as all pharmaceutically acceptable salts of such compounds. The phrase "a compound of Formula I" includes all subgeneric groups of Formula I including Formula II, III, an so forth, as well as all forms of such compounds, including salts and hydrates, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound of the invention), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

A dash ("-") that is not between two letters or symbols is used to indicate a point of attachment for a substituent. For example, —(CH$_2$)C$_3$-C$_8$cycloalkyl is attached through carbon of the methylene (CH$_2$) group.

"Alkanoyl" indicates an alkyl group as defined herein, attached through a keto (—(C=O)—) bridge. Alkanoyl groups have the indicated number of carbon atoms, with the carbon of the keto group being included in the numbered carbon atoms. For example a C$_2$alkanoyl group is an acetyl group having the formula CH$_3$(C=O)—.

"Alkyl" is a branched or straight chain saturated aliphatic hydrocarbon group, having the specified number of carbon atoms, generally from 1 to about 12 carbon atoms. The term C$_1$-C$_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. C$_1$-C$_6$alkyl, C$_1$-C$_4$alkyl, and C$_1$-C$_2$alkyl. When C$_0$-C$_n$ alkyl is used herein in conjunction with another group; for example, (cycloalkyl) C$_0$-C$_4$alkyl, the indicated group, in this case cycloalkyl, is either directly bound by a single covalent bond (C$_0$), or attached by an alkyl chain having the specified number of carbon atoms, in this case 1, 2, 3, or 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. When "C$_0$-C$_n$alkoxy" is used in with another group, for example, (heteroaryl)C$_0$-C$_4$ alkoxy, the indicated group, in this case heteroaryl, is either attached via a covalently bound oxygen bridge (C$_0$alkoxy), or attached by an alkoxy group having the specified number of carbon atoms, in this case from 1 to about 4 carbon atoms, that is covalently bound to the group it substitutes via the alkoxy oxygen atom.

The term "alkylester" indicates an alkyl group as defined herein attached through an ester linkage. The ester linkage may be in either orientation, e.g. a group of the formula —O(C=O)alkyl or a group of the formula —(C=O)Oalkyl. The carbonyl carbon of the ester is not included in the indicated number of carbon atoms in the alkyl chain.

"Cycloalkyl" is a saturated hydrocarbon ring group, having the specified number of carbon atoms. Monocyclic cycloalkyl groups typically have from 3 to about 8 carbon ring atoms or from 3 to 7 (3, 4, 5, 6, or 7) carbon ring atoms. Cycloalkyl substituents may be pendant from a substituted nitrogen or carbon atom, or a substituted carbon atom that may have two substituents may have a cycloalkyl group, which is attached as a spiro group. Examples of cycloalkyl groups include cyclopropyl, cyclobutyl, cyclopentyl, or cyclohexyl as well as bridged or caged saturated ring groups such as norbornane or adamantane.

The terms "(cycloalkyl)C$_0$-C$_n$alkyl" indicates a substituent in which the cycloalkyl and alkyl are as defined herein, and the point of attachment of the (cycloalkyl)alkyl group to the molecule it substitutes is either a single covalent bond, (C$_0$alkyl) or on the alkyl group. (Cycloalkyll)alkyl encompasses, but is not limited to, cyclopropylmethyl, cyclohexylmethyl, and cyclohexylmethyl.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Halo" or "halogen" indicates any of fluoro, chloro, bromo, and iodo.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

"Mono- and/or di-alkylcarboxamide" indicates a monoalkylcarboxamide group of formula (alkyl$_1$)—NH—(C=O)— or a dialkylcarboxamide group of the formula (alkyl$_1$)(alkyl$_2$)—N—(C=O)— in which the point of attachment of the mono- or dialkylcarboxamide substituent to the molecule it substitutes is on the carbon of the carbonyl group. The term "mono and/or di-alkylcarboxamide" also includes groups of the formula (alkyl$_1$)(C=O)NH— and (alkyl$_1$)(C=O)(alkyl$_2$)N— in which the point of attachment is the nitrogen atom. The groups alkyl$_1$ and alkyl$_2$ are independently chosen alkyl groups having the indicated number of carbon atoms.

"Mono- and/or di-alkylcarbamate" indicates a mono-alkylcarbamate group of formula (alkyl$_1$)—NH—(C=O)O— or a dialkylcarboxamide group of the formula (alkyl$_1$)(alkyl$_2$)—N—(C=O)O— in which the point of attachment of the mono- or dialkylcarbamte substituent to the molecule it substitutes is on the oxygen of the carbonyl group. The term "mono and/or di-alkylcarbamate" also includes groups of the formula (alkyl$_1$)O(C=O)NH— and (alkyl$_1$)O(C=O)(alkyl$_2$)N— in which the point of attachment is the nitrogen atom. The groups alkyl$_1$ and alkyl$_2$ are independently chosen alkyl groups having the indicated number of carbon atoms.

"Mono- and/or di-alkylsulfonamide" is a mono-alkyl group of formula (alkyl$_1$)-NH—SO$_2$— or a di-alkyl group of the formula (alkyl$_1$)—N(alkyl$_2$)—SO$_2$— in which the point of attachment of alkylsulfonamide substituent to the molecule it substitutes is on the sulfur of the sulfonyl group. The term "mono and/or di-alkylcarboxamide" also includes groups of the formula (alkyl$_1$)(SO$_2$)NH— and (alkyl$_1$)(SO$_2$)(alkyl$_2$)N— in which the point of attachment is the nitrogen atom. The groups alkyl$_1$ and alkyl$_2$ are independently chosen alkyl groups having the indicated number of carbon atoms.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

Unless otherwise specified substituents are named into the core structure. For example, it is to be understood that when (cycloalkyl)alkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions of the invention refers to a diluent, excipient, or vehicle with which an active compound is provided.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment," as used herein includes providing a compound of Formula I, either as the only active agent or together with at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of Formula I, as the only active agent or together with at least one additional active agent to a patient having or susceptible to a hepatitis C infection.

A "therapeutically effective amount" of a pharmaceutical combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roch TaqMan assay. In certain preferred embodiments treatment reduces HCV RNA levels below the limit of quantitation (30 IU/mL, as measured by the Roche TaqMan(R) assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where $p<0.05$.

Chemical Description

Formula I includes all subformulae thereof. In certain situations, the compounds of Formula I may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $U_1$, $U_2$, $V_1$, $V_2$, $Z_1$, $Z_2$, $R_1$, $R_3$, $R_4$, A, $A_2$, n, and m. Unless otherwise specified, each variable within such a formula is defined independently of other variables. Thus, if a group is said to be substituted, e.g. with 0-2 $R^*$, then the group may be substituted with up to two $R^*$ groups and $R^*$ at each occurrence is selected independently from the definition of $R^*$. Also, combinations of substituents and/or variables are permissible only if such combinations result in stable compounds.

This disclosure includes compounds of Formula I and the pharmaceutically acceptable salts thereof.

Formula I

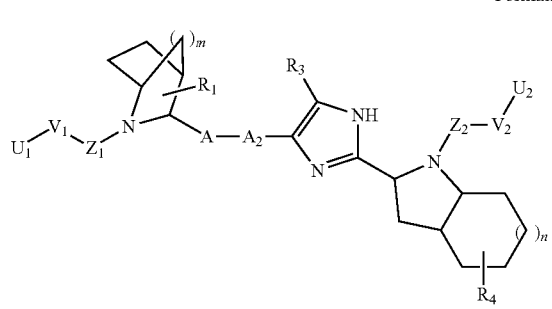

The variables, e.g., $U_1$, $U_2$, $V_1$, $V_2$, $Z_1$, $Z_2$, $R_1$, $R_3$, $R_4$, A, $A_2$, n, and m, carry the definitions set forth in the "Summary" section.

In addition to compounds of Formula I as described above, this disclosure also includes compounds of Formula I in which one or more of the following conditions is met for the variables Formula I. The disclosure includes compounds of Formula I-VI (Formula II thru VI are subgeneric groups Formula of I) that carry any combination of the variable definitions set forth below that results in a stable compound.

Formula II

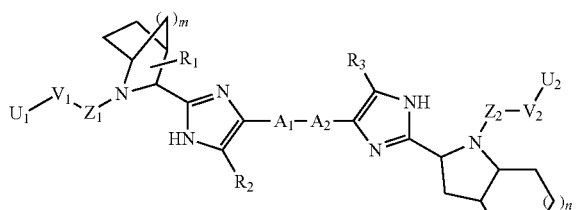

Formula III

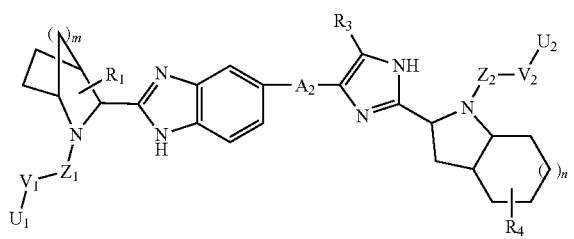

Formula IV

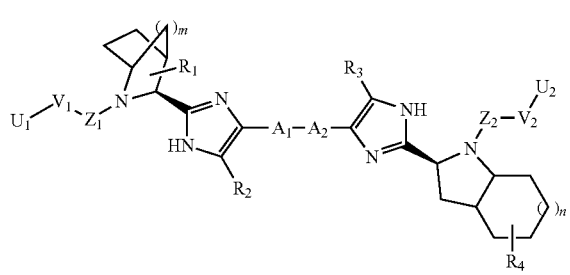

Formula V

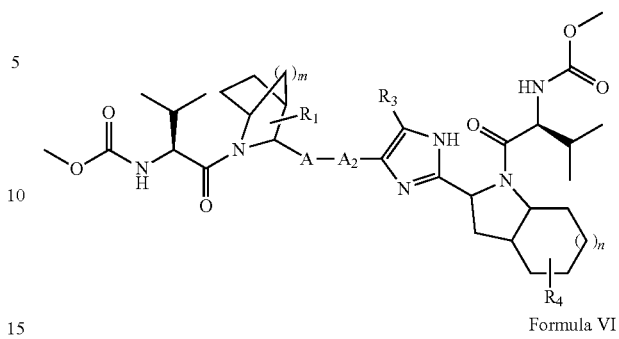

Formula VI

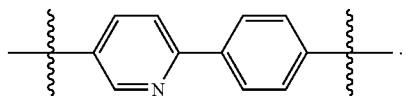

Also included in this disclosure are compounds of Formula I, wherein one or more of the following conditions is met.

(1) m and n are both 1.
(2) m is 2 and n is 1.
(3) R1 and R4 are absent.
(4) $R_2$ and $R_3$ are both hydrogen or methyl.
(5) $A_1$ and $A_2$ are both phenyl, each of which phenyl is unsubstituted or substituted with one or more substituents independently chosen from hydroxyl, halogen, $C_1$-$C_2$alkyl, $C_1$-$C_2$alkoxy, mono- and di-$C_1$-$C_2$alkylamino, trifluormethyl, and trifluoromethoxy.
(6) One of $A_1$ and $A_2$ is phenyl and the other of $A_1$ and $A_2$ is pyridyl, each of which $A_1$ and $A_2$ is unsubstituted or substituted with one or more substituents independently chosen from hydroxyl, halogen, $C_1$-$C_2$alkyl, $C_1$-$C_2$alkoxy, mono- and di-$C_1$-$C_2$alkylamino, trifluormethyl, and trifluoromethoxy.
(7) $A_1$ and $A_2$ are both pyridyl, each of which phenyl is unsubstituted or substituted with one or more substituents independently chosen from hydroxyl, halogen, $C_1$-$C_2$alkyl, $C_1$-$C_2$alkoxy, mono- and di-$C_1$-$C_2$alkylamino, trifluormethyl, and trifluoromethoxy.
(8) -$A_1$-$A_2$- is a group of the formula:

(9) $Z_1$ and $Z_2$ are both —(C=O)—.
(10) $V_1$ and $V_2$ are independently chosen $C_1$-$C_2$alkylene, each of which is substituted with one or more substituents independently chosen from $C_1$-$C_6$alkyl and ($C_3$-$C_6$cycloalkyl)$C_0$-$C_2$alkyl.
(11) $U_1$ and $U_2$ are independently hydrogen, or mono- and di-$C_1$-$C_6$alkylcarbamate, mono- and di-$C_1$-$C_6$alkylcarboxamide, mono- and di-$C_1$-$C_6$alkylsulfonamide.
(12) Compounds of Formula I, II, IV and VI in which n is 1, $R_1$ and $R_4$ are absent, $R_2$ and $R_3$ are independently selected from hydrogen and methyl, and $A_1$ and $A_2$ are independently chosen from phenyl and pyridyl.

Also included herein are the following specific compounds and their salts:

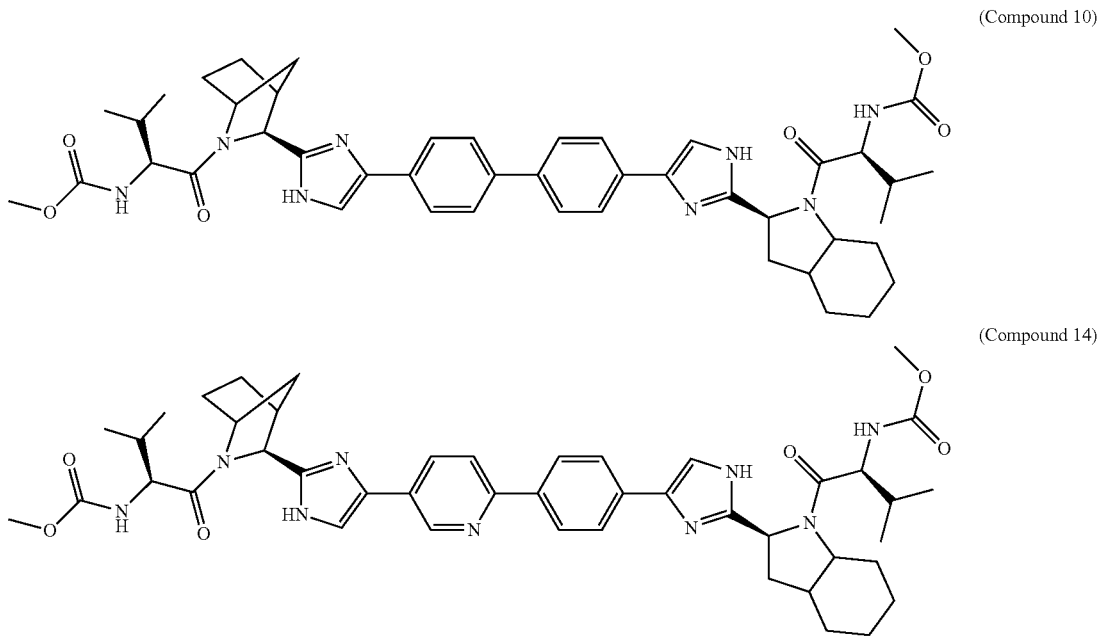

(Compound 10)

(Compound 14)

Pharmaceutical Preparations

Compounds of the invention can be administered as the neat chemical, but are preferably administered as a pharmaceutical composition. Accordingly, the invention provides pharmaceutical compositions comprising a compound or pharmaceutically acceptable salt of the Formula I, together with at least one pharmaceutically acceptable carrier. The pharmaceutical composition may contain a compound or salt of Formula I as the only active agent, or may contain one or more additional active agents.

Compounds of the invention may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions can be formulated for oral administration. These compositions contain between 0.1 and 99 weight % (wt. %) of a hydrazone or a diacyl hydrazine compound and usually at least about 5 wt. % of a hydrazone or a diacyl hydrazine compound. Some embodiments contain from about 25 wt. % to about 50 wt. % or from about 5 wt. % to about 75 wt. % of the hydrazone or diacyl hydrazine compound.

Methods of Treatment

The invention includes methods of preventing and treating hepatitis C infections, by providing an effective amount of a compound of the invention to patient at risk for hepatitis C infection or infected with a hepatitis C virus. A compound of the invention may be provided as the only active agent or may be provided together with one or more additional active agents.

The pharmaceutical combinations disclosed herein are useful for preventing and treating hepatitis C infections in patients.

An effective amount of a pharmaceutical combination of the invention may be an amount sufficient to (a) prevent hepatitis C or a symptom of a hepatitis C from occurring in a patient who may be predisposed to hepatitis C but has not yet been diagnosed as having it or prevent diseases that may be associated with or caused by a primary hepatitis C infection (such as liver fibrosis that can result in the context of chronic HCV infection); (b) inhibit the progression of hepatitis C; and (c) cause a regression of the hepatitis C infection. An amount of a pharmaceutical composition effect to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

The invention also includes using pharmaceutical combinations comprising a compound of the invention in prophylactic therapies. In the context of prophylactic or preventative treatment an effective amount of a compound of the invention is an amount sufficient to significantly decrease the patient's risk of contracting a hepatitis C infection.

The invention includes a method of inhibiting HCV replication in vivo comprising providing a compound or salt of the invention to a patient infected with HCV a concentration of the compound or salt sufficient to inhibit HCV replicon replication in vitro. In this instance the concentration includes an in vivo concentration, such as a blood or plasma concentration. The concentration of compound sufficient to inhibit HCV replicon replication in vitro includes may be determined from an assay of replicon replication such as the assay provided in Example 5, herein.

Methods of treatment include providing certain dosage amounts of a compound of the invention to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration. Dosage unit a compound of the invention. In certain embodiments 25 mg to 500 mg, or 25 mg to 200 mg of a compound of the invention are provided daily to a patient. Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

Packaged Formulations

The invention comprises providing a compound or salt of Formula I in a container together with instructions for using the composition to treat a patient suffering from Hepatitis C infection.

The invention includes packaged pharmaceutical combinations. Such packaged combinations include a compound of Formula I in a container. The container may additionally include instructions for using the combination to treat or prevent a viral infection, such as a hepatitis C infection, in a patient.

The packaged pharmaceutical combination may include one or more additional active agents.

Combination Methods

The invention includes pharmaceutical compositions and methods of treatment in which a compound or salt of the invention is provided together with one or more additional active agents. In certain embodiments the active agent (or agents) is an HCV protease inhibitor or HCV polymerase inhibitor. For example the protease inhibitor may be telaprevir (VX-950) and the polymerase inhibitor may be valopicitabine, or NM 107, the active agent which valopicitabine is converted into in vivo. In certain embodiments the second active agent is ribavirin, interferon, or Peg-interferon alpha conjugate. In certain embodiments the second active agent is ACH-1625, ACH-2684, or ACH-3102.

Preferred combinations include combinations of a compound of Formula I of this disclosure, including Compound 10, 14, or 15, and a second active agent chosen from any of the following.

(A) A compound as shown and described in U.S. Pat. No. 7,906,619, issued 15 Mar. 2011 which is hereby incorporated by reference at columns 3-5, for its teachings regarding Formula I of the '619 patent, and at columns 67-82 for its disclosure of NS5a inhibitor compounds.

(B) A compound as shown and described in US Patent Application US 2010/0216725, published 26 Aug. 2010 from U.S. patent application Ser. No. 12/635,270, filed 10 Dec. 2009, which is hereby incorporated by reference at pages 25-98 for its disclosure of compounds 13 and 38-257.

(C) A compound as shown and described in US Patent Application US 2010/0152103, published 17 Jun. 2010 from U.S. patent application Ser. No. 12/635,049, filed 10 Dec. 2009, which is hereby incorporated by reference at pages 22-58 for its disclosure of compounds 24, 34-35 and 42-136.

(D) A compound as shown and described in U.S. Provisional Patent Application 61/567,216, filed 6 Dec. 2011, which is hereby incorporated by reference at paragraphs

[0011]-[0026] for its teachings regarding Formula I of the '216 application, and at pages 34-43, for its teachings regarding compound II and the compounds shown in Example 3.

In certain embodiments it is preferred that the second active agent is chosen from the following compounds and salts thereof disclosed in U.S. Pat. No. 7,906,619: (2S,4R)-1-((S)-2-tert-butyl-4-oxo-4-(piperidin-1-yl)butanoyl)-N-(1-(cyclopropylsulfonylcarbamoyl)-2-vinylcyclopropyl)-4-(7-methoxy-2-phenylquinolin-4-yloxy)pyrrolidine-2-carboxamide; (2R,6R,13aS,14aR,16aS,Z)-N-(cyclopropylsulfonyl)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide; (2R,6R,13aR,14aS,16aS,Z)-N-(cyclopropylsulfonyl)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide; and (2S,4R)-1-(S)-2-tert-butyl-4-oxo-4-(piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide.

In other embodiments the second active agent is chosen from the following compounds and salts thereof disclosed in US Patent Appl. No. 2010/0152103: (2R,6R,13aS,16aS,Z)-N-(cyclopropylsulfonyl)-5,16-dioxo-6-(2-oxo-2-(4-(trifluoromethyl)piperidin-1-yl)ethyl)-2-(2-(pyridin-2-yl)-8,9-dihydro-7H-cyclopenta[h]quinolin-4-yloxy)-1,2,3,5,6,7,8,9,10,11,13a,14,14a,15,16,16a-hexadecahydrocyclopropa[e]pyrrolo[1,2-a][1,4]diazacyclopentadecine-14a-carboxamide; (2R,6R,14aR,16aS,Z)-N-(cyclopropylsulfonyl)-2-(2-(4-isopropylthiazol-2-yl)-7-methoxy-8-methylquinolin-4-yloxy)-5,16-dioxo-6-(2-oxo-2-(4-(trifluoromethyl)piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide; (2R,6R,14aR,16aS,Z)-N-(cyclopropylsulfonyl)-6-(2-(3,3-difluoropiperidin-1-yl)-2-oxoethyl)-2-(2-(4-isopropylthiazol-2-yl)-7-methoxy-8-methylquinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; (2R,6R,14aR,16aS,Z)-N-(cyclopropylsulfonyl)-6-(2-(3,3-difluoropiperidin-1-yl)-2-oxoethyl)-2-(7-methoxy-8-methyl-2-(pyridin-3-yl)quinolin-4-yloxy)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; (2R,6R,14aR,16aS,Z)-2-(5-chloro-6-methoxy-3-(pyridin-2-yl)isoquinolin-1-yloxy)-N-(cyclopropylsulfonyl)-6-(2-(3,3-difluoropiperidin-1-yl)-2-oxoethyl)-5,16-dioxo-1,2,3,5,6,7,8,9,10,11,13a,14,14a,15,16,16a-hexadecahydrocyclopropa[e]pyrrolo[1,2-a][1,4]diazacyclopentadecine-14a-carboxamide; (2R,6R,14aR,16aS,Z)-N-(cyclopropylsulfonyl)-2-(7-methoxy-8-methyl-2-(pyridin-3-yl)quinolin-4-yloxy)-5,16-dioxo-6-(2-oxo-2-(4-(trifluoromethyl)piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide; and (2R,6R,14aR,16aS,Z)-2-(5-chloro-6-methoxy-3-(pyridin-2-yl)isoquinolin-1-yloxy)-N-(cyclopropylsulfonyl)-5,16-dioxo-6-(2-oxo-2-(4-(trifluoromethyl)piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide.

According to the methods of the invention, the compound of the invention and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound of The invention and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments method of treatment includes providing a patient with a compound of Formula I and an interferon such as a pegylated interferon or interferon gamma. The interferon may be the only compound provided with the compound of the invention or may be provided with an additional active agent that is not an interferon.

The invention methods of treatment and pharmaceutical combinations including compounds of the invention any one or combination of the following compounds and substances as an additional active agent:

Anti-fibrotics: IP-501 (InterMune)

Caspase Inhibitors: IDN-6556 (Idun Pharmaceuticals) and GS-9450 (Gilead)

Cyclophilin Inhibitors: for example, NIM811 (Novartis), SCY-635 (Scynexis), and DEBIO-025 (Debiopharm);

Cytochrome P450 monooxygenase inhibitors: ritonavir, ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497 (Merimebodib). Preferred CYP inhibitors include ritonavir, ketoconazole, troleandomycin, 4-methylpyrazole, cyclosporin, and clomethiazole;

Glucocorticoids: hydrocortisone, cortisone, prednisone, prednisolone, methylprednisolone, triamcinolone, paramethasone, betamethasone, and dexamethasone.

HCV Protease Inhibitors: for example ACH-1625 and ACH-2684. U.S. Pat. No. 7,906,619 is hereby incorporated for its teachings regarding anti-HCV compounds. U.S. patent application Ser. No. 12/635,270 at pages 52-167 and Ser. No. 12/635,049 at pages 43-92 are hereby incorporated by reference for their teachings regarding anti-HCV compounds, ACH 1625 and ACH 2684 (Achillion), ABT-450 (Abbott), ACL-181 and AVL-192 (Avila), BI-335 (Boehringer Ingelheim), BMS-032 (Bristol Meyers Squibb), boceprevir (Merck), TMC-435, MK-7152 (Merck), GS-9256 (Gilead), GS-9451 (Gilead), R7227 (Intermune), VX-500 (Vertex), VX-950 (telaprevir, Vertex), VX-985 (Vertex), TMC-435 (Tibotec), GW-433908 (prodrug of Amprenavir, Glaxo/Vertex), indinavir (CRIXIVAN, Merck), ITMN-191 (Intermune/Array Biopharma), BILN 2061 (Boehringer-Ingelheim), TMC435350 (Tibotec/Medivir), BI 201335 (Boehringer Ingelheim), PHX-1766 (Phenomix), MK-7009 (Merck), narlaprevir (SCH900518, Schering)

Hematopoietins: hematopoietin-1 and hematopoietin-2. Other members of the hematopoietin superfamily such as the various colony stimulating factors (e.g. (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha n1 from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering),interferon beta-1a (REBIF, Ares-Serono, Inc. and Pfizer), consensus interferon alpha (INFERGEN, Intermune), interferon gamma-1b (ACTIMMUNE, Intermune, Inc.), un-pegylated interferon alpha, alpha interferon, and its analogs, and synthetic thymosin alpha 1 (ZADAXIN, SciClone Pharmaceuticals Inc.), and lamdba interferon (BMS)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (HEPX-C, XTL), HuMax-HepC (Genmab), Hepatitis C Immune Globin (human) (CIVACIR, Nabi Biopharmaceuticals), XTL-002 (XTL), Rituximab (RITUXAN, Genentech/IDEC)

Nucleoside analogues: IDX-184 (Idenix), PSI-7977 and PSI-938 (Pharmasset), INX-189 (Inhibitex), R7128 (Roche), R7348 (Roche), GS-6620 (Gilead), TMC-649 (Tibotec), Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), isatoribine (Anadys Pharmaceuticals), ANA971(Anadys Pharmaceuticals), ANA245 (Anadys Pharmaceuticals), and viramidine (ICN), an amidine prodrug of ribavirin. Combinations of nucleoside analogues may also be employed.

Non-nucleoside inhibitors: PSI-6130 (Roche/Pharmasset), ABT-333 and ABT-072 (Abbott), delaviridine (RESCRIPTOR, Pfizer), PF-868554 (Pfizer), GSK-852 (GlaxoSmithKline), IDX-325 (Idenix), ANA-598 (Anadys), VX-222 and VX-759 (Vertex), MK-3281 (Merck), BI-127 (Boehringer Ingelheim), BMS-325 (Bristol Meyers), and HCV-796 (Viropharm)

NS4a inhibitors: for example ACH-1095. US patent application no. US2007/0004711 is hereby incorporated by reference in its entirety for its teachings regarding HCV inhibitors and U.S. patent application Ser. No. 12/125,554 at pages 45-90 is hereby incorporated by reference for its teachings regarding HCV inhibitors.

NS4b inhibitors: clemizole (Arrow Therapeutics)

NS5a inhibitors: A-382 (Arrow Therapeutics), BMS-790052 (BMS)

NS5b inhibitors: INX-181, IDX-375, MK-3281, PSI-7977, PSI-7851, PSI-938, RG-9190, VX-222 (Vertex), and BMS-791325 (Bristol Meyers Squibb).

P7 protein inhibitor: amantadine (SYMMETREL, Endo Pharmaceuticals, Inc.)

Polymerase inhibitors: Filibuvir (PF-00868554, Pfizer), NM283 (valopicitabine) (Idenix), JTK 003 (AKROS Pharma), HCV-796 (ViroPharma/Wyeth), IDX184 (Idenix), VCH-916 (Vertx), R7128 (PSI6130, Roche), R1626 (Roche), MK-3281 (Merck), PSI-7851 (Pharmasset), ANA598 (Anadys), BI207127 (Boehringer-Ingelheim), GS 9190 (Gilead).

RNA interference: SIRNA-034 RNAi (Sirna Therapeutics) and ISI 14803 (Isis Pharmaceutical/Elan)

Therapeutic Vaccines: IC41 (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), TLR7 agonist (Anadys Pharmaceuticals), CPG10101(Coley), and TLR9 agonists including CPG 7909 (Coley).

Vaccines: HCV/MF59 (Chiron), IC41 (Intercell), E-1 (Innogenetics)

Patients receiving hepatitis C medications are typically given interferon together with another active agent. Thus methods of treatment and pharmaceutical combinations in which a compound of The invention is provided together with an interferon, such as pegylated interferon alfa 2a, as the additional active agents are included as embodiments. Similarly methods and pharmaceutical combinations in which ribavirin is an additional active agent are provided herein.

EXAMPLES

Abbreviations

The following chemical abbreviations are used in the Examples below. Additional abbreviations used in these examples will be familiar to those of skill in the art of organic chemical synthesis.

AcOK Potassium Acetate

DCM Dichloromethane

DIEA N,N-Diisopropylethyl amine

DMF Dimethyl formamide

EDCI 3-Ethyl-1 (N,N-dimethyl)aminopropylcarbodiimide

EtOAc Ethyl Acetate

HOBt Hydroxybenzotriazole $NH_4Oac$ Ammonium Acetate

Pd(dppf) 1,1'-Bis(diphenylphosphino)ferrocene]dichloropalladium(II)

$Pd(Ph_3)_4$ Tetrakis(triphenylphosphine)palladium(0)

Example 1
Synthetic Example 1
Synthesis of Compound 10
Reaction Scheme 1
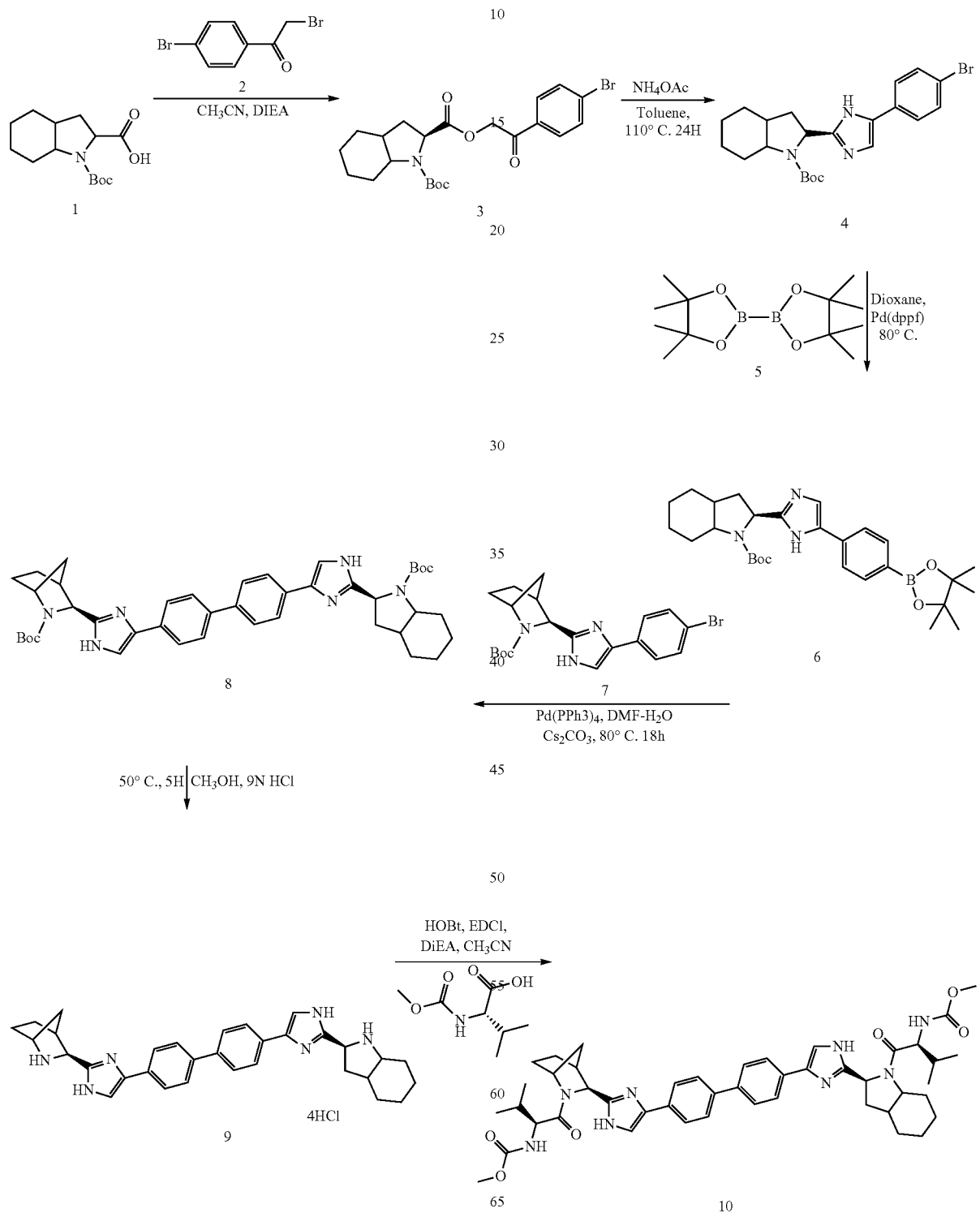

Step 1. Preparation of (2S)-2-(2-(4-bromophenyl)-2-oxoethyl) 1-tert-butyl hexahydro-1H-indole-1,2(2H, 3H)-dicarboxylate (3)

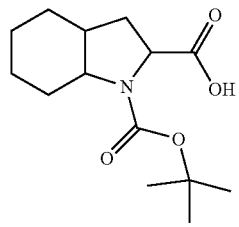
1

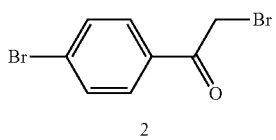
2

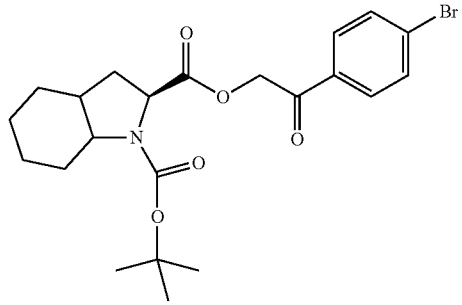
3

DIEA (0.65 mL, 1.05 eq) in acetonitrile (20 mL) is slowly added, at 5° C., to a mixture of 1 (1.07 g, 1.05 eq) and 2 (1.056 g, 1.0 eq). The mixture is then stirred for 4 h at RT. The reaction mixture solvent is removed in vacuo. $CH_2Cl_2$ (50 mL) is added to the residue. The residue is washed with water, 1N Citric acid aq., and then water and $NaHCO_3$ aq. The residue is dried over $Na_2SO_4$ and evap. The crude product is used directly used in the next reaction.

Step 2. Preparation of (2R)-tert-butyl 2-(5-(4-bromophenyl)-1H-imidazol-2-yl)octahydro-1H-indole-1-carboxylate (4)

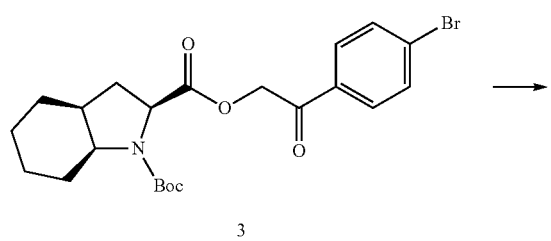
3

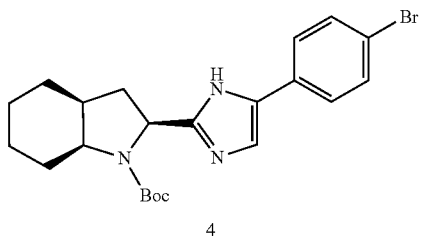
4

Compound 3 (1.1 g) and $NH_4OAc$ (3.08 g, 10 eq) in toluene (30 mL) are refluxed for 18 h then cooled to 5° C. $NaHCO_3$ solution is added and the organic layer is washed with $Na_2CO_3$ aq. (~20 mL). The toluene layer is washed with brine and purified by chromatography using DCM/EtOAc to get 4 (700 mg).

Step 3. Preparation of (2S)-tert-butyl 2-(5-(4-(4,4,5,5-tetramethyl-1,3,2-dioxaborolan-2-yl)phenyl)-1H-imidazol-2-yl)octahydro-1H-indole-1-carboxylate (6)

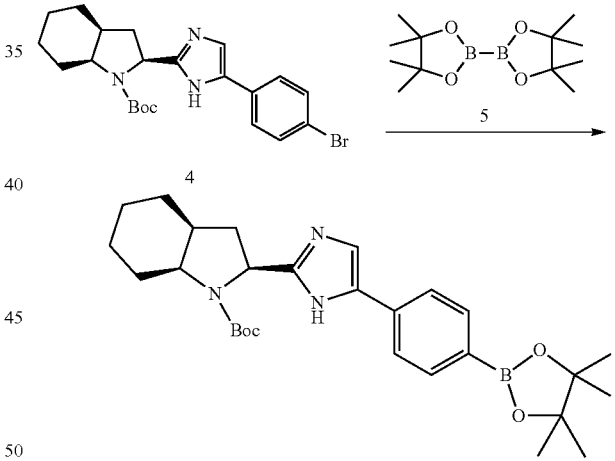

Compound 4 (445 mg), 5 (506 mg, 2 eq) and AcOK (490 g) in dioxane (25 mL) was bubbled with Ar (~10 min) and then added Pd-dppf (65 mg, 8 mol %) and then bulled Ar (~0.10 min). The reaction mixture was stirred for 20 h at 80° C. (oil bath temp). The reaction mixture was cooled to r.t and filtered to remove any solid and filtrate was removed solvent. The residue was washed with $NaHCO_3$ aq and ext with DCM then removed solvent. The residue was purified by chromatography using DCM/EtOAc to get 6 (500 mg)

Step 4. (2S)-tert-butyl 2-(4-(4'-(2-((3S)-2-(tert-butoxycarbonyl)-2-azabicyclo[2.2.1]heptan-3-yl)-1H-imidazol-4-yl)biphenyl-4-yl)-1H-imidazol-2-yl)octahydro-1H-indole-1-carboxylate (8)

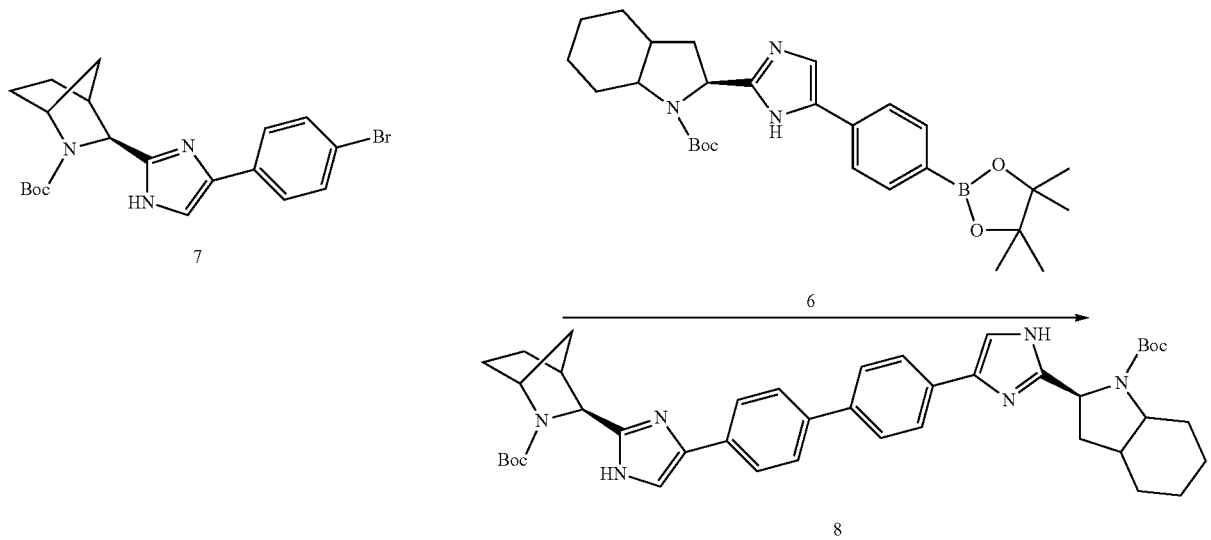

Compounds 7 (84 mg, 0.2 mmol) and 6 (110 mg, 0.25 mmol) are dissolved in DMF (9 ml) and 1 ml water. $Cs_2CO_3$ (130 mg, 0.4 mmol, 2 eq.) is then added to this solution. The resulting reaction mixture is purged with argon for 15 min. Tetrakis (triphenylphosphine) palladium (15 mg) is then added. The reaction mixture is stirred for 18 h at 80° C. (oil bath temp) under argon. Completion of the reaction is determined by HPLC monitoring. The reaction mixture is then cooled to RT. This reaction mixture is added to 100 ml of 13% NaCl solution. A white solid precipitates, and the reaction mixture is stirred for another 30 min at RT. The precipitate is filtered, washed with water, and dried. Crude compound 8 is used in the next reaction, without further purification.

Step 5. (2S)-2-(4-(4'-(2-((3S)-2-azabicyclo[2.2.1]heptan-3-yl)-1H-imidazol-4-yl)biphenyl-4-yl)-1H-imidazol-2-yl)octahydro-1H-indole (9)

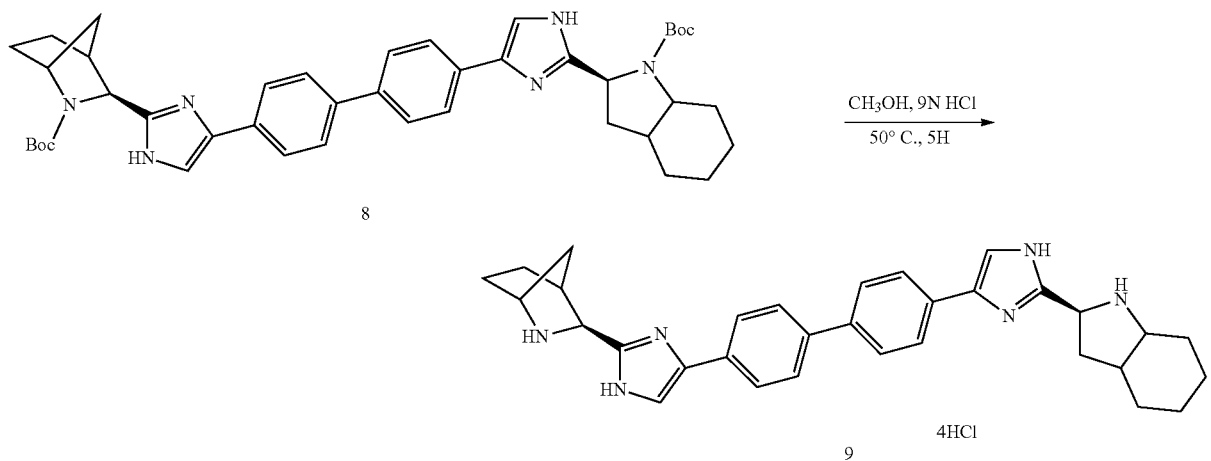

Compound 8 were taken in 9 ml methanol; 1 ml Conc. HCL and 0.2 ml water was added. Resulting reaction was stirred for 5 h at 50° C. (oil bath temp) completed, after completion of the reaction monitor by HPLC. The resulting slurry was cooled to RT and held with agitation for about 1H. Filtration of the slurry afforded a solid; washed with 15 ml acetone dried directly used in the next reaction.

Step 6. Preparation of Compound 10

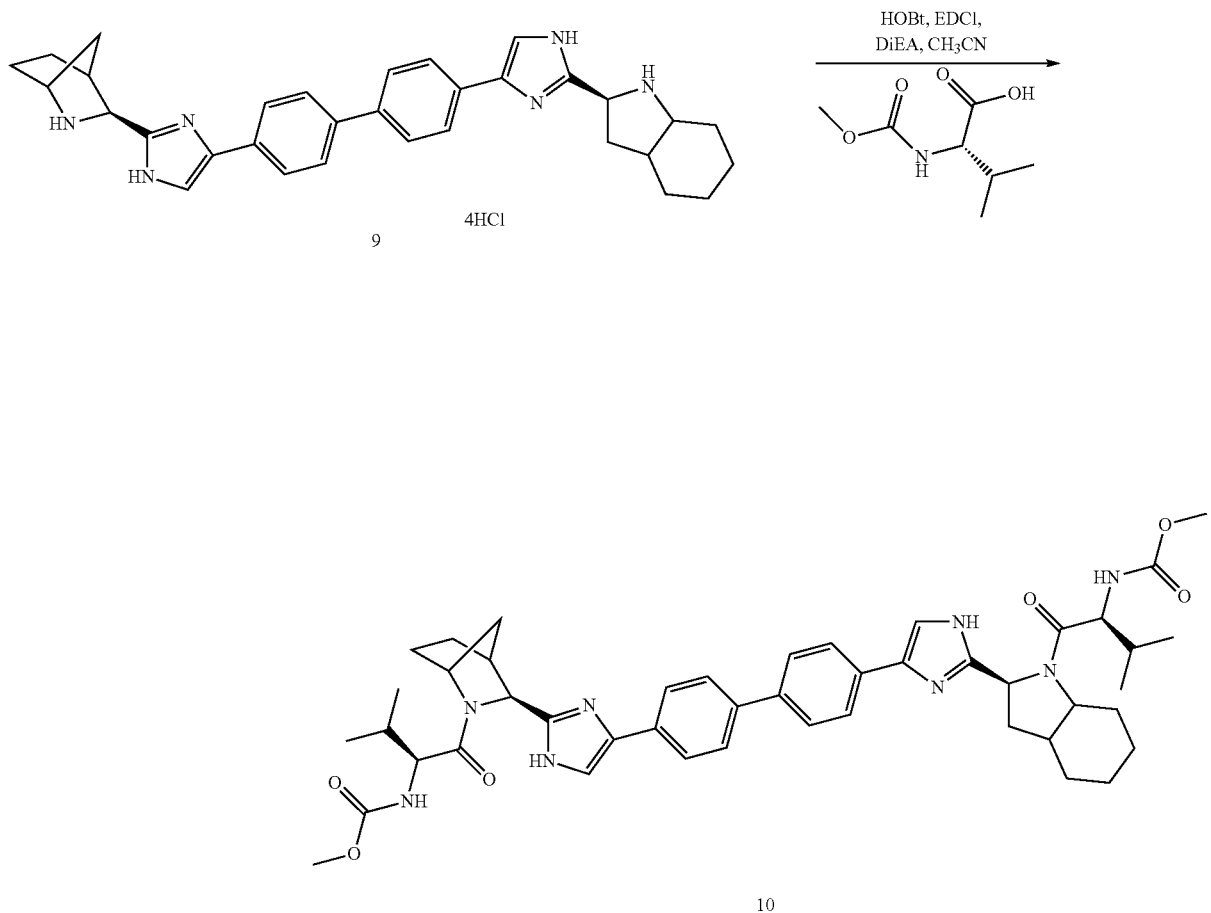

Moc-Val (105 mg, 3 eq) and HOBt (90 mg, 3.125 eq) in Acetonitrile (10 mL) are added to and EDCI-HCl (115 mg, 3.0 eq) solution, stirred for 1 h, and then cooled to 5° C. Compound 9 (0.2 mmol), then added DIEA (0.167 ml, 5 eq) are added slowly to this mixture. The reaction mixture is removed from the ice bath and stirred for room temperature for 24 h. 13% NaCl aq. (10 mL) and added EtOAc (30 ml mL) are added to the reaction mixture and the mixture is extracted. The organic layer is separated and washed with 0.5N NaOH in 13% NaCl aq. The organic layer is washed again with 13% NaCl aq (20 mL) and water, filtered and concentrated. The residue was added EtOH (10 mL). 1.24M HCl in EtOH (0.250 mL) is added and heated for 1 h at 50° C. (out). The solvent is removed and the product is precipitated from 5% EtOH and acetone to yield 97% pure compound. The precipitate is collected by filtration, washed with acetone (5 mL), and dried. MS: 819 ($M^+$+1), Retention time 1.53 (ACPGEN).

Example 2
Preparation of Compound 14
Compound 14 is prepared using the above procedure. MS: 820 (M$^+$+1) Retention tithe: 1.56 (ACPGEN). Scheme 2 shows the synthetic method for compound 14.
Reaction Scheme 2
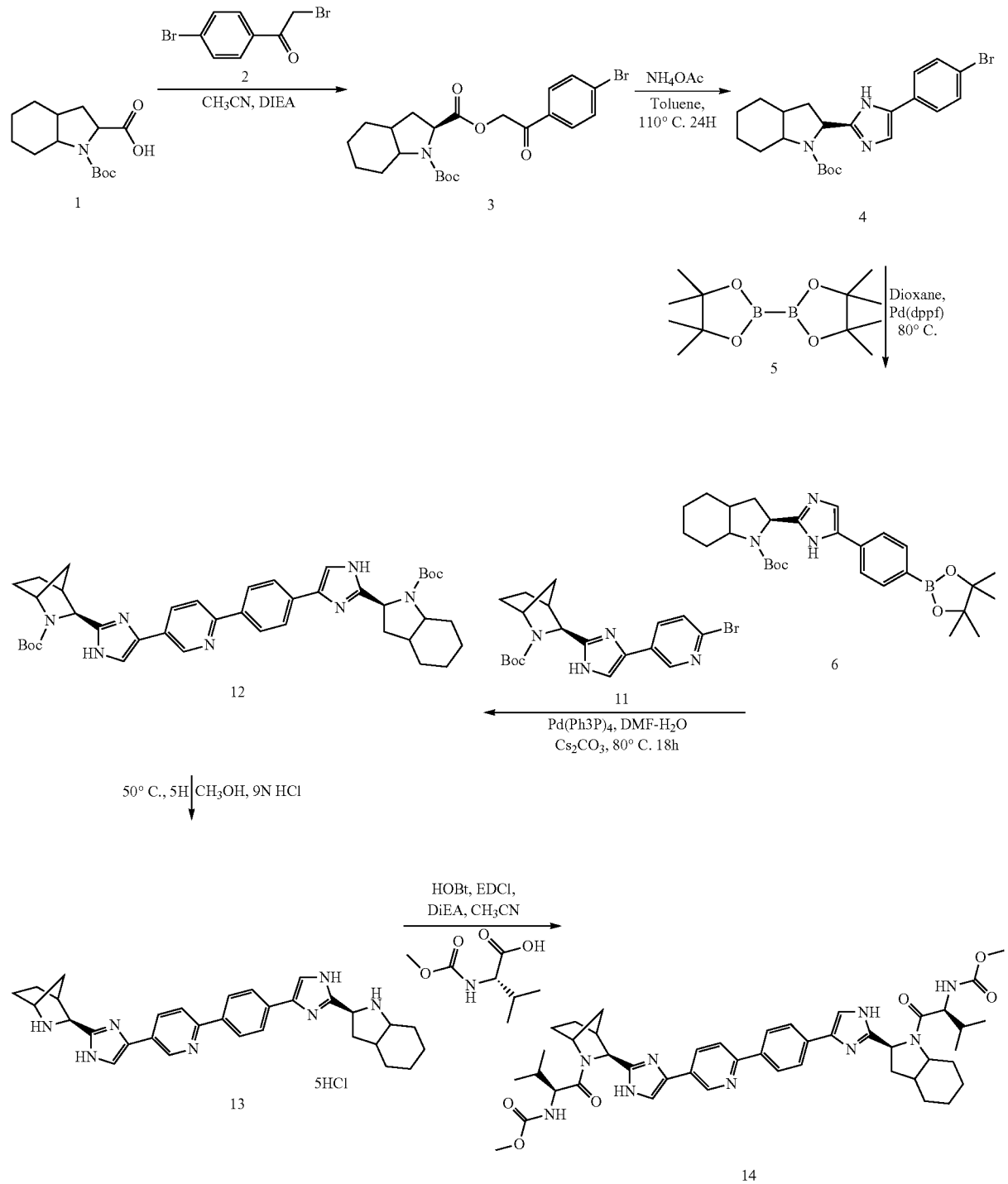

Example 3
Additional Compound
The following compound was made by the methods disclosed in Examples 1 and 2. Minor changes in reaction conditions and starting materials, which will be readily apparent to those of skill in the art, were made to produce the disclosed compound.
Compound 15:
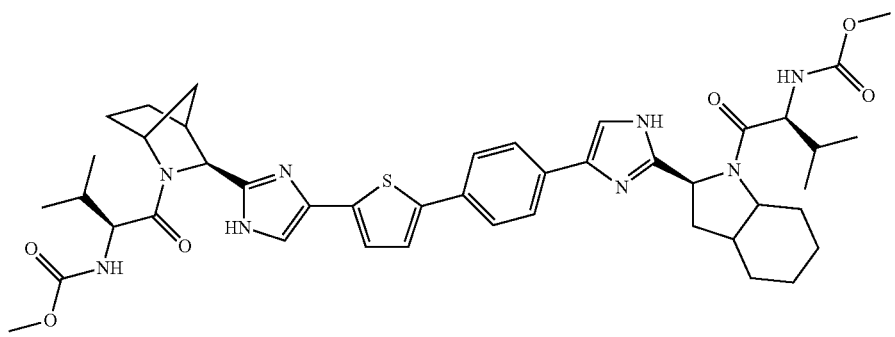
Example 4
Synthesis of Compounds 21 and 22
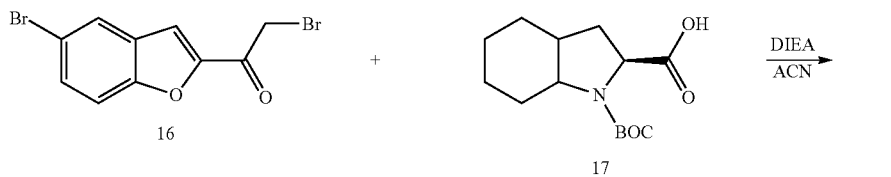
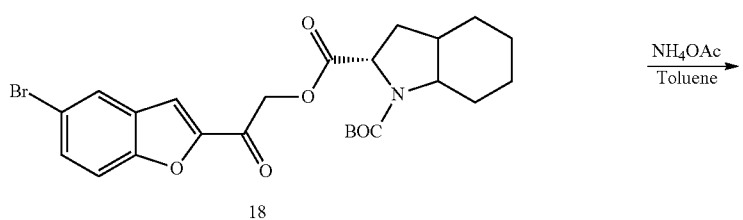
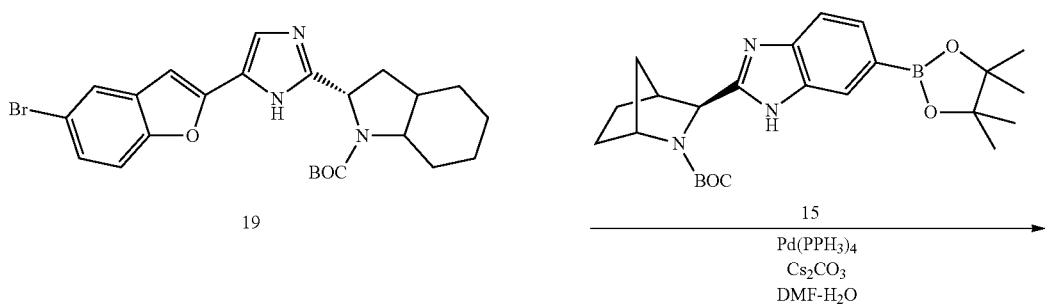

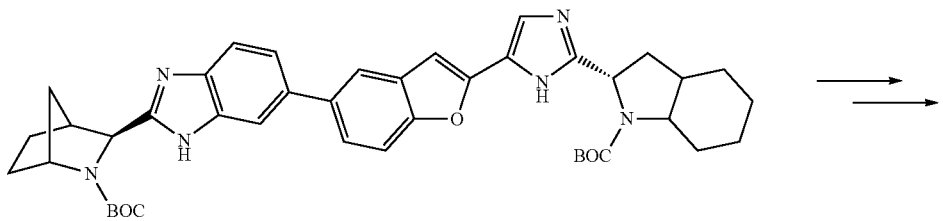

20

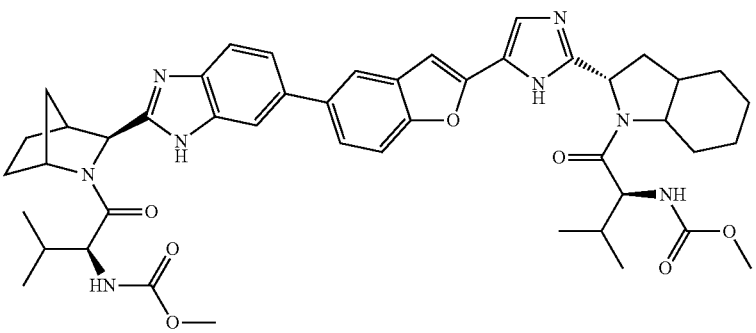

21

Step 1. Preparation of Compound 15

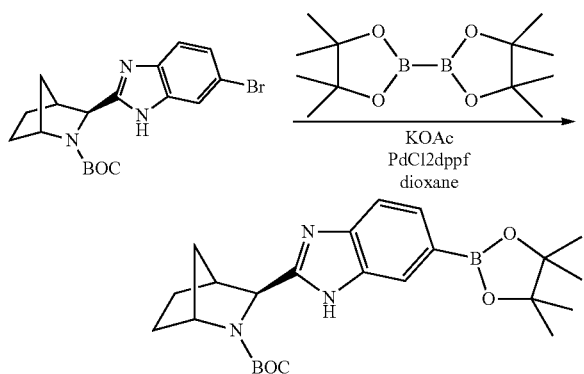

Into a mixture of bromide (1.02 g, 2.60 mmol), bis(pinacolato)diboron (1.32 g, 5.2 mmol)*, and KOAc (0.76 g, 7.8 mmol) in anhydrous dioxane (25 ml), argon was bubbled through for 10 min with stirring. Add Pd(dppf)Cl$_2$ (0.212 g, 0.26 mmol) and keep bubbling Ar through for additional 10 min. The mixture was then heated in an 80-90° C. oil bath under Ar with stirring overnight till the reaction was complete. Concentration followed by typical aq work up with AcOEt extraction gave crude. The pure product was obtained by silica gel column chromatography with DCM/MeOH 10/1 as eluent.

Step 2. Preparation of Compound 21

The synthesis of 21 was carried out as depicted in Scheme 2. Into commercially available bromoketone 16 (333 mg, 1.04 mmol) and Boc-Oic-OH 17 (296 mg, 1.1 mmol) mixed in acetonitrile (10 ml), add DIEA (0.191 ml, 1.1 mmol) at room temperatures with stirring. After reaction completed overnight, water (40 ml) was added. Typical aq. workup with AcOEt extraction gave product 18 as pale yellow powder (547 mg). Compound 18 was treated with NH$_4$OAc (800 mg, 10.4 mmol) in refluxed toluene (20 ml) overnight. The mixture was washed with sodium bicarbonate solution, water, and brine and dried over Na$_2$SO$_4$. After evaporation, imidazole compound 19 was obtained as yellow solid for next step. Compound 19 (88.8 mg, 0.183 mmol), compound 15 (96 mg 0.22 mmol) and Cs$_2$CO$_3$ (119 mg, 0.366 mmol) were mixed in DMF-water (5 ml-0.5 ml). The mixture was de-oxygenated by bubbling in argon gas for 10 min. After adding catalyst Pd(PPh$_3$)$_4$ (11 mg, 0.009 mmol), the mixture was heated at 80° C. overnight with stirring. After typical aq work up with AcOEt extraction, the crude was applied to silica gel column chromatography with DCM/MeOH 10/1 as eluent to give compound 20 (84.8 mg, 64%). The final compound 21 was then prepared with general procedures of de-BOC and coupling of MOC-Val as appeared elsewhere.

Compound 22: was made by the methods disclosed in Example 4. Minor changes in reaction conditions and starting materials, which will be readily apparent to those of skill in the art, were made to produce Compound 22.

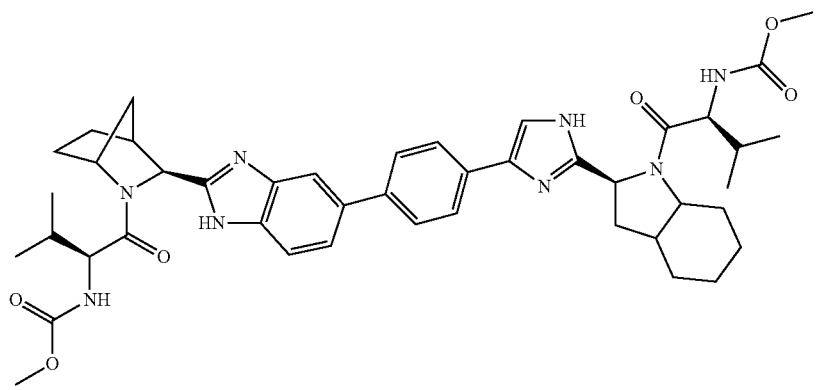 [SMILES: COC(=O)N[C@H](C(=O)N1C2CCC(C2)[C@H]1c1nc2cc(-c3ccc(-c4c[nH]c([C@@H]5CC6CCCCC6N5C(=O)[C@@H](NC(=O)OC)C(C)C)n4)cc3)ccc2[nH]1)C(C)C]

Example 5

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

5A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no AJ242652).

The replicon is transfected into Huh-7 cells using standard methods such as electroporation.

5B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu—N1 1, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1:4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×10$^5$ cells/10 ml/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

5C. Treatment of HCV-Replicon Containing Cells with Test Compound

HCV replicon-containing cells are rinsed with once PBS once; 2 mls of trypsin are then added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418

(50 mg/ml, BRL catalog #10131-035), 5 ml MEM non-essential amino acids (100×BRL #11140-050) and 5 ml pen-strep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 fcells/100 μl/well of 96 well plate (6-7.5×10⁵ cells/10 ml/plate). Plates are placed into 37° C. 5% $CO_2$ incubator overnight.

5D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 μl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 μl of PBS. The PBS is then decanted and the plates tapped in a paper towel to remove any remaining PBS. Cells are fixed in situ with 100 μl/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 μl of blocking solution (10% FBS; 3% NGS in PBS) for 30 minutes at room temperature. The blocking solution is removed and 100 μl of rabbit anti-NPTII diluted 1:1000 in blocking solution is added to each well. The plates are then incubated 45-60 minutes at room temperature. After incubation, wells are washed six times with PBS-0.05% Tween-20 solution. 100 μl of 1:15,000 diluted Europium (EU)-conjugated goat anti-rabbit in blocking buffer is added to each well and incubated at room temperature for 30-45 minutes. The plates are washed again and 100 μl of enhancement solution (Perkin Elmer #4001-0010) is added to each well. Each plate is shaken (approx. 30 rpm) in a plate shaker for three minutes. 95 μl is transferred from each well to a black plate; the EU signal is quantitated in a Perkin-Elmer VICTOR plate reader (EU-Lance).

When tested in this assay Compounds 10 and 14-15 exhibit EC50 values of less than 10 nanomolar.

Example 6

Cytotoxicity Assays

To insure that the decrease in replicon replication is due to compound activity against the HCV replicon rather than non-specific toxicity assays are used to quantitate compound cytotoxicity.

6A. Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

6B. MTS Assay for Cytotoxicity

Cell viability may also be determined by CELLTITER 96 AQUEOUS ONE Solution Cell Proliferation Assay (Promega, Madison Wis.), a colorimetric assay for determining the number of viable cells. In this method, before fixing the cells, 10-20 μl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Albumin and MTS methods for determining cytotoxicity may be obtained as follows: Cells are treated with different concentrations of test compound or Helioxanthin for a three day-period. Prior to lysis for detection albumin as described above, the MTS reagent is added according to manufacturer's instruction to each well and incubate at 37° C. and read at OD 490 nm. The cellular albumin quantitation is then performed as described above.

What is claimed is:

1. A compound of Formula I or a pharmaceutically acceptable salt thereof,

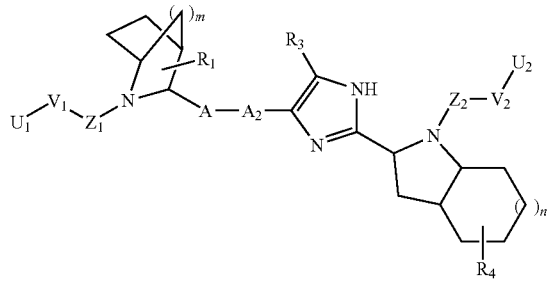

Formula I wherein:
m is 1 or 2;
n is 0, 1, or 2;
where A is a group of the formula

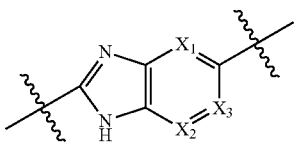

or

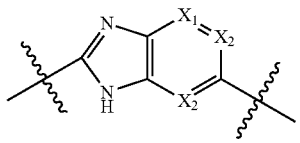

where $X_1$, $X_2$, and $X_3$ are independently N or CH, where each CH is unsubstituted or substituted with a substituent independently chosen from hydroxyl, halogen, $C_1$-$C_2$alkyl, and $C_1$-$C_2$alkoxy;

where $A_2$ is chosen from phenyl, pyridyl, thienyl, benzylfuranyl, and pyrimidinyl, each of which is unsubstituted or substituted with one or more substituents independently chosen from amino, cyano, hydroxyl, halogen, $C_1$-$C_6$alkyl, $C_1$-$C_6$alkoxy, mono- and di-$C_1$-$C_4$alkylamino, $C_1$-$C_2$haloalkyl, and $C_1$-$C_2$haloalkoxy;

$U_1$ and $U_2$ are independently chosen from hydrogen, $C_2$-$C_6$alkanoyl, $C_1$-$C_6$alkylester, mono- and di-$C_1$-$C_6$alkylcarbamate, mono- and di-$C_1$-$C_6$alkylcarboxamide, mono- and di-$C_1$-$C_6$alkylsulfonamide, and $C_1$-$C_6$alkylsulfonamide; each of which $U_1$ and $U_2$ other than hydrogen is unsubstituted or substituted with 1 or more substituents independently chosen from amino, cyano, hydroxyl, halogen, mono- and di-$C_1$-$C_4$alkylamino, $C_1$-$C_4$alkoxy, $C_1$-$C_2$haloalkyl, and $C_1$-$C_2$haloalkoxy;

$V_1$ and $V_2$ are independently chosen $C_1$-$C_4$alkylene, each of which is unsubstituted or substituted with one or more substituents independently chosen from amino, cyano, hydroxyl, halogen, $C_1$-$C_6$alkyl, $C_1$-$C_6$alkoxy, mono- and di-$C_1$-$C_4$alkylamino, ($C_3$-$C_7$cycloalkyl)$C_0$-$C_4$alkyl, $C_1$-$C_2$haloalkyl, and $C_1$-$C_2$haloalkoxy;

$Z_1$ and $Z_2$ are independently chosen from —$SO_2$—, —$NHSO_2$—, —(C=O)—, —(C=O)O—, —NH—, and —(C=O)NH—, each of which may be in either orientation;

$R_1$ is absent or $R_1$ is one or more substituents independently chosen from hydroxyl, halogen, $C_1$-$C_2$alkyl, and $C_1$-$C_2$alkoxy;

$R_3$ is chosen from hydrogen, from hydroxyl, halogen, $C_1$-$C_2$alkyl, and $C_1$-$C_2$alkoxy;

$R_4$ is absent or $R_4$ is one or more substituents present on either ring of the bicyclic system on which it is shown, which substituents are independently chosen from hydroxyl, halogen, $C_1$-$C_2$alkyl, and $C_1$-$C_2$alkoxy.

2. A compound or salt of claim 1 of Formula III:

Formula III

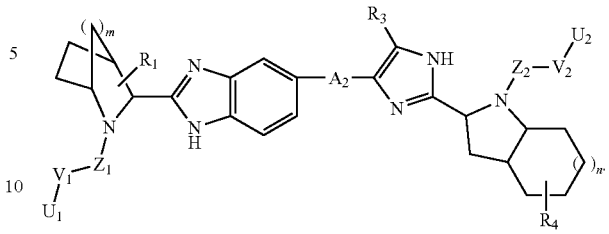

3. A compound or salt of claim 1, where m and n are both 1.

4. A compound or salt of claim 1, where m is 2 and n is 1.

5. A compound or salt of claim 3, wherein $R_1$ and $R_4$ are absent.

6. A compound or salt of claim 1, wherein $R_3$ is hydrogen or methyl.

7. A compound or salt of any one of claim 1 wherein $Z_1$ and $Z_2$ are both —(C=O)—.

8. A compound or salt of claim 1, wherein $V_1$ and $V_2$ are independently chosen $C_1$-$C_2$alkylene, each of which is substituted with one or more substituents independently chosen from $C_1$-$C_6$alkyl and ($C_3$-$C_6$cycloalkyl)$C_0$-$C_2$alkyl.

9. A compound or salt of any one of claim 1, wherein:

$U_1$ and $U_2$ are independently hydrogen, or mono- and di-$C_1$-$C_6$alkylcarbamate, mono- and di-$C_1$-$C_6$alkylcarboxamide, mono- and di-$C_1$-$C_6$alkylsulfonamide.

10. A compound or salt of claim 1 of Formula V:

Formula V

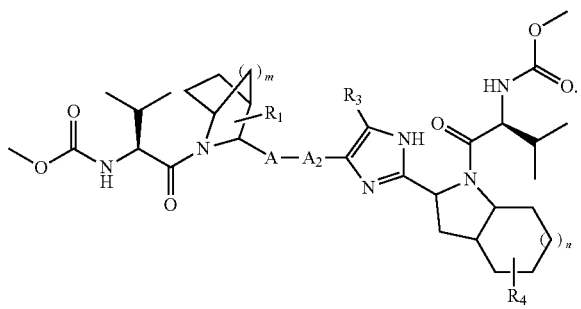

11. A compound or salt of claim 1, wherein the compound has the formula

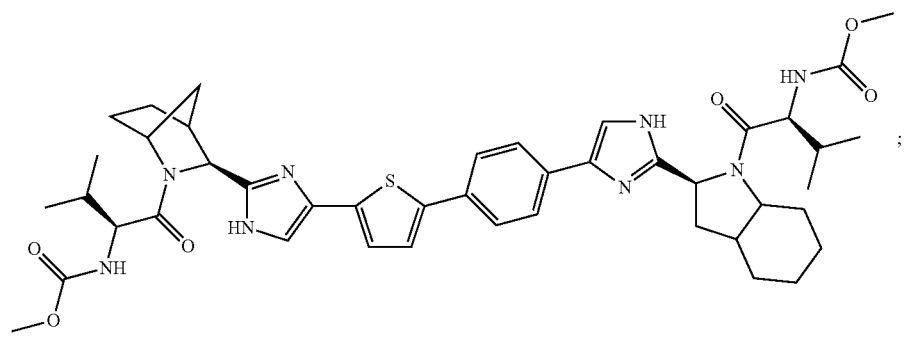

;

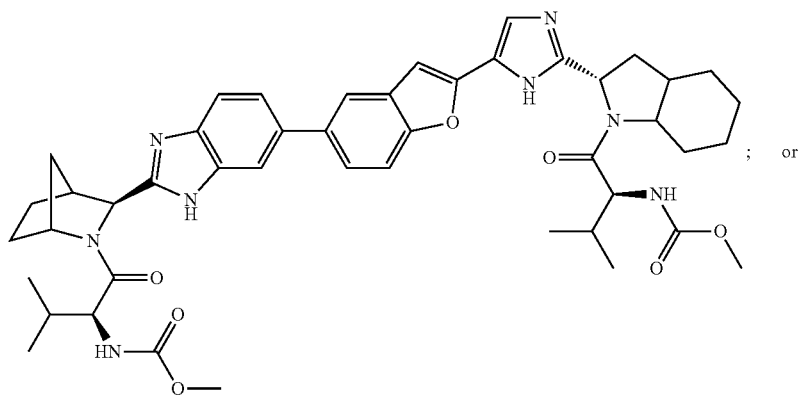

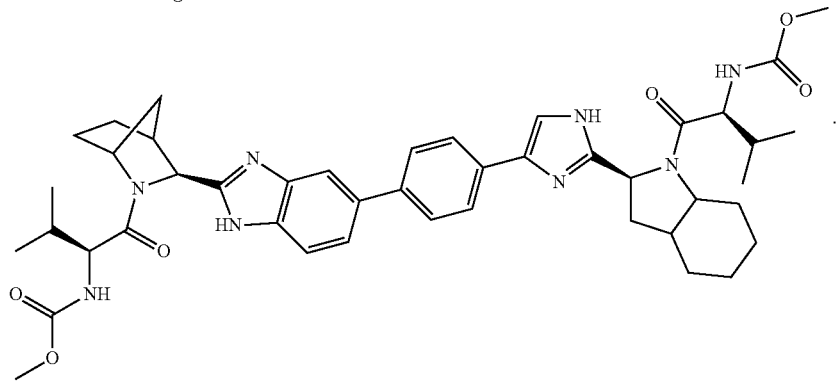

12. A pharmaceutical composition comprising a therapeutically effective amount of a compound or salt of claim 1, and at least one pharmaceutically acceptable carrier.

13. The pharmaceutical composition of claim 12, wherein the composition comprises a second active agent.

14. A method of treating hepatitis C infection in a patient, comprising providing a therapeutically effective amount of one or more compounds of claim 1 to a patient in need thereof.

* * * * *

UNITED STATES PATENT AND TRADEMARK OFFICE
CERTIFICATE OF CORRECTION

| | |
|---|---|
| PATENT NO. | : 8,835,456 B1 |
| APPLICATION NO. | : 13/423935 |
| DATED | : September 16, 2014 |
| INVENTOR(S) | : Jason Allan Wiles et al. |

It is certified that error appears in the above-identified patent and that said Letters Patent is hereby corrected as shown below:

TITLE PAGE: ITEM (75)

Name of inventor is spelled incorrectly on the face of the patent. The correct spelling is Venkat Gadhachanda.

Signed and Sealed this
Tenth Day of February, 2015

Michelle K. Lee
*Deputy Director of the United States Patent and Trademark Office*